United States Patent [19]
Durville et al.

[11] Patent Number: 6,039,729
[45] Date of Patent: Mar. 21, 2000

[54] PORTABLE CAUTERY SYSTEM

[75] Inventors: Frederick M. Durville, Chelmsford; Raymond J Connolly, Pembroke; John C Lantis, Somerville; Robert H Rediker, Watertown; Steven D. Schwaitzberg, Canton, all of Mass.

[73] Assignees: Cynosure, Inc.; N. E. Medical Center Hospitals, both of Mass.

[21] Appl. No.: 08/910,949

[22] Filed: Aug. 8, 1997

[51] Int. Cl.⁷ ..................................................... A61B 17/32
[52] U.S. Cl. .................................. 606/16; 606/13; 606/28
[58] Field of Search ................................ 606/2, 8, 9, 10, 606/13, 15, 16, 27, 28, 29, 41, 205, 206, 210

[56] References Cited

U.S. PATENT DOCUMENTS

| | | | |
|---|---|---|---|
| 3,980,861 | 9/1976 | Fukunaga | 606/28 |
| 4,587,968 | 5/1986 | Price | 606/28 |
| 5,147,356 | 9/1992 | Bhatta | 606/2 |
| 5,300,065 | 4/1994 | Anderson | 606/8 |
| 5,306,274 | 4/1994 | Long | 606/16 |
| 5,336,221 | 8/1994 | Anderson | 606/8 |
| 5,342,358 | 8/1994 | Daikuzono | 606/15 |
| 5,464,436 | 11/1995 | Smith | 606/9 |
| 5,470,331 | 11/1995 | Daikuzono | 606/16 |
| 5,484,436 | 1/1996 | Eggers et al. | 606/41 |

*Primary Examiner*—Linda C. M. Dvorak
*Assistant Examiner*—Bryan K. Yarnell
*Attorney, Agent, or Firm*—Don Halgren

[57] ABSTRACT

A medical instrument, such as a cautery device, wherein bleeding is stopped or prevented by clamping the bleeding site with a dedicated forceps and using a highly localized heat source such as a fiber-coupled laser. The laser energy quickly and locally heats up the tip of the forceps cautery device. The tip of the forceps device has minimum thermal mass and is thermally insulated from the body of the forceps. In this present invention, there is no electrical current flowing through or into the tip of the instrument, and can therefore be safely used in any part of the body including around the heart or the brain. When combined with a small semiconductor laser, the device is battery operated, self-contained and hand-held, and can therefore be used in any environment including outdoors.

14 Claims, 4 Drawing Sheets

2

PORTABLE CAUTERY SYSTEM

This invention was made with government support under contract F29601-95-C-0050 awarded by the USAF Phillips Laboratory, Kirkland AFB, N. Mex. 87117-6008. The government has certain rights in the invention.

BACKGROUND OF THE INVENTION

1. Field of the Invention

This invention relates to portable cautery devices, and more particularly to cautery devices powered by laser arrangements.

2. Prior Art

Hemostasis, the stopping or prevention of blood loss, is a matter of urgent concern in many areas of clinical medicine including surgery, trauma and obstetrics. If not stopped in a timely manner, severe bleeding leads to certain death. Bleeding can be caused by accidental conditions during a trauma, or during surgery where tissue and vessels have to be cut to have access to the target site or to remove an organ or local tissue. Small bleeding can usually be stopped using simple means, but more intense bleeding is more difficult to stop. Intense bleeding is the prevalent cause of death following severe trauma such as bullet or stab wounds.

An electro-cautery device is usually used by doctors and surgeons during surgery to stop or prevent the bleeding, or they can also simply tie the blood vessel when the bleeding is too intense and the source can be localized. The electro-cautery device is based on the use of radio-frequency electrical current to cauterize the bleeding site. This implies the use of high voltage electrical energy, which can be sometimes more harmful than the bleeding itself when used in certain areas of the human body such as the brain or the heart. In such areas of the human body, the electro-cautery device can not be used to stop undesirable bleeding. The electro-cautery device is efficient only on small vessels of less than approximately 1.5 mm. diameter, and is inefficient on intense bleeding typically found in severe trauma situations such as bullet or stab wounds. The electro-cautery equipment also requires the availability of a utility current source such as 110 or 220 VAC, and therefore is not portable and cannot be used outdoors.

Direct laser energy can also be utilized to cauterize bleeding tissues. However, current operating room practice in laser cautery and laser ablation requires burdensome procedures made necessary by the fact that laser devices are constructed in such a manner that the laser light is visible to the surgeons and nurses conducting the procedure. To protect against injury from laser, medical personnel must wear protective eyewear to protect their eyes from light injury. Such protective eyewear are particularly burdensome as they are unusually heavily tinted and therefore, thus also interfering with good viewing of the patient and body tissue of the patient during an operation. The tint of protective eyewear, necessary to block laser light, creates a low contrast field of view which makes it difficult to distinguish between different types of body tissue.

In the present invention, we teach of a novel method and construction of a preferred embodiment to stop or prevent the bleeding under any condition, including in proximity of the heart or the brain, or in absence of a utility electrical supply such as in outdoors environment. The medical procedure to stop bleeding using this invention is very similar to standard procedures commonly practiced by doctors and surgeons. A dedicated medical forceps is used to clamp the bleeding site or local blood vessel(s) and thus temporarily stops or prevents the bleeding. The tip of the forceps is then locally and quickly heated up by a localized heat source such as small electric heater or a fiber-coupled infrared laser beam to such a temperature that the tissue and vessels within the clamped area are cauterized and welded together. This process efficiently closes all the local vessels, thereby stopping and/or preventing the bleeding.

Animal studies on live, anesthetized rabbits have demonstrated the efficacy of the device and procedure. Various vessels in the mesentery tissue of the small intestine of the rabbits are quickly and effectively cauterized using this invention. The studies have also shown that this invention can effectively cauterize large vessels such as the Aorta of a rabbit, which could not be cauterized with the electro-cautery system.

In this invention, no electrical current is flowing through the tip of the instrument thereby eliminating any risk of electrical shock when used around the heart or the brain of a patient. The energy delivered to the tip of the instrument is entirely contained within the tip and results in essentially no collateral damage to surrounding tissues. The energy necessary to heat up the tip of the instrument can be generated by a small and efficient infrared semiconductor laser. The infrared laser beam is then delivered to the tip of the instrument through a small optical fiber and absorbed by the tip. The device can be battery operated, self-contained and can easily be hand-held, and therefore can be used in any environment or in places where no utility electrical source is available such as outdoors.

The present invention provides for a completely shielded laser transmission path. The laser fiber optic conductor is housed within an opaque heating tip, thus preventing the leakage of laser light from the instrument into the operating room. Other procedures for the present invention, include the welding together of body tissue. A dedicated medical forceps may be utilized to clamp and hold together the body tissues to be welded together. The tip of the forceps may then be locally and quickly heated up to a localized heat source such as a small electric heater or a fiber-coupled infrared laser beam to such a temperature that the tissues within the clamped area are welded together. A further embodiment of the present invention includes the use of such a device to cut and dissect tissues. For example, by activating the device for longer duration at the desired temperature, the tip of these instruments may be utilized to vaporize the tissue contained between the clamped section, while the tissue immediately adjacent the clamped section is heated to such a temperature so as to coagulate that tissue, thus providing simultaneous cutting and coagulation action.

The animals involved in the development of this invention were procured, maintained, and used in accordance with the Federal Animal Welfare Act and the Guide for Care and Use of Laboratory Animal, prepared by the Institute of Laboratory Animal Resources—National Research Council. The animal experiments were performed at NEMC, which is fully accredited by the AAALAC. The protocol was approved by NEMC Animal Research Committee and USAF Human/Animal Use Committee.

BRIEF SUMMARY OF THE INVENTION

In the present invention, a medical instrument such as a forceps is combined with a highly localized heat source to provide a portable cautery device which avoids delivery of electrical, radio wave or electromagnetic energy to the body tissue, to permit that cautery device to be utilized in electrical/RF sensitive areas of a body. In a first embodiment, a heat source is provided by a stand-alone laser generator coupled into a small fiber in communication with the forceps device. In a second embodiment, the medical forceps device itself is directly attached to a small battery operated infrared semiconductor laser. In yet another embodiment, the heat source is provided by a small electric heater. In the use of this cauterizing device, the highly localized heat source provides a rapid local heating of the tip of the medical instrument, thereby permitting a cauterizing of a bleeding vessel and/or tissue in a sensitive area.

The medical instrument of the present invention, such as a forceps, has tips arranged to minimize its thermal mass and minimize heat losses. In a preferred embodiment of the present invention, the tips may be made of Titanium metal having dimensions of about 2 mm by 2 mm by 8 mm. The tips may be coated with a PFA Teflon coating to minimize the sticking of the cauterized tissue onto the tip. Each tip is preferably mounted on a thermal insulation block. The block is arranged to provide thermal insulation between the metal tip and the body of the forceps. The thermally insulated tip may be arranged to be easily removable and disposable. The removability of the tip permits the cautery device to be easily cleaned and sterilized.

The cautery device of the present invention is utilized to provide hemostasis in the human body during surgical procedures or in severe trauma situations. It may be used in a manner similar to that of a typical bi-polar electrocautery device. After visual location of the bleeding site or local vessel(s), the surrounding tissue is grabbed and clamped with the tips of the dedicated forceps. This provides a temporary hemostasis at the targeted site. The device is then activated for a duration of typically 5 seconds or until traditional visual clues such as local bubbling and popping indicate that the targeted site is effectively cauterized. When the device is activated, the tip of the dedicated forceps is quickly heated up to such a temperature, as for example, to about 200° C., so as to effectively cauterize and weld the clamped tissue and blood vessels contained between the pair of tips of the forceps, thus providing hemostasis at this site. The procedure can be repeated as many times as needed to provide hemostasis at all the desired sites. The procedure can also be repeated several times at the same site if necessary. The activation time can be increased or decreased to provide appropriate hemostasis at the targeted site. Larger vessels or more intense bleeding requires longer activation time.

The present invention thus comprises a cautery forceps system for the cauterization of sensitive body tissue to avoid delivery of electrical, RF and/or electromagnetic energy thereto, including a forceps having a pair of biasable fingers, each of the fingers having a distal end with a metal tip secured thereon, at least one of the tips having a bore therein, the bore having an open end and a closed end. An optical conduit, the distal end of which is mounted within the bore in the metal tip, and facing the closed end thereof. A source of optical energy such as supplied from a laser generator, is coupled to the optical conduit to provide actuatable heat so as to raise the temperature of the metal tip on at least one of the fingers to permit the forceps to cauterize, weld or cut body tissue. The metal tip is disposed within an insulated jacket, the insulated jacket being attached to the distal end of the finger. The fingers of the forceps each have a proximal end, each proximal end of the fingers being attached to a housing, the housing also enclosing the source of the laser energy. The forceps are removable from the housing to permit the forceps free movement with respect to the housing. The metal tips of the forceps are removable from the distal end of the fingers. The tips of the forceps are preferably made of Titanium metal.

The invention also includes a method of providing hemostasis on body tissue using a thermo-cautery device comprising the steps of clamping the targeted blood vessels and/or body tissue between a pair of thermally insulated, heatable metal tips of a forceps device; and heating at least one of the metal tips of the forceps device by a supply of energy directed through a conduit from an energy generator, so as to avoid delivery of electrical, RF or electro-magnetic energy to body tissue during cauterization, welding or cutting thereof. The method includes the steps of generating heating of the metal tips in the forceps, by a laser pulse from a laser generator, into the tips, and directing the laser pulse through an optical fiber, which comprises the conduit. The method includes the steps of absorbing the laser pulse in the metal tip; and converting the laser pulse into heat within the metal tip. The method also includes the steps of attaching an insulative jacket to the metal tip, and attaching the insulative jacket to a distal end of a finger of the forceps device, and energizing the forceps device by biasing the fingers of the device towards a tissue to be cauterized, so as to trigger a switch on the fingers during the biasing action.

The invention thus also comprises a thermo-dissector system for the simultaneous dissection and coagulation of body tissues to prevent direct delivery of electromagnetic energy including electrical, RF or optical energy to the tissues, comprising a cutting instrument having a body portion with a proximal end and a distal end. The distal end of the body portion has a sharp metal tip edge or point member, and a thermal insulator arranged between the body portion and the metal point member. The body portion and the metal point member have a bore communicating therethrough, the bore having a closed distal end in the metal point member. An optical conduit is arranged in the bore in abutting relationship with the distal end of the bore, and an actuatable source of energy is coupled to the optical conduit to provide a heat energy so as to raise the temperature of the metal tip edge or point member to permit the vaporization and dissection of tissue while simultaneously coagulating those dissected tissues.

The invention includes a coagulating instrument having a holding body and the metal tip having a smooth surface thermally insulated from the holding body of the instrument, with a bore therethrough, to a closed end, an optical conduit having a distal end arranged in the closed end of the bore in the metal tip; and a source of optical energy coupled to the optical conduit to provide actuatable heat so as to raise the temperature of the metal tip to permit the metal tip to locally coagulate tissues.

BRIEF DESCRIPTION OF THE DRAWINGS

The foregoing and other objects, features and advantages of the invention will be apparent when viewed in conjunction with the following drawings, in which.

DESCRIPTION OF THE PREFERRED EMBODIMENTS

Figure 1:
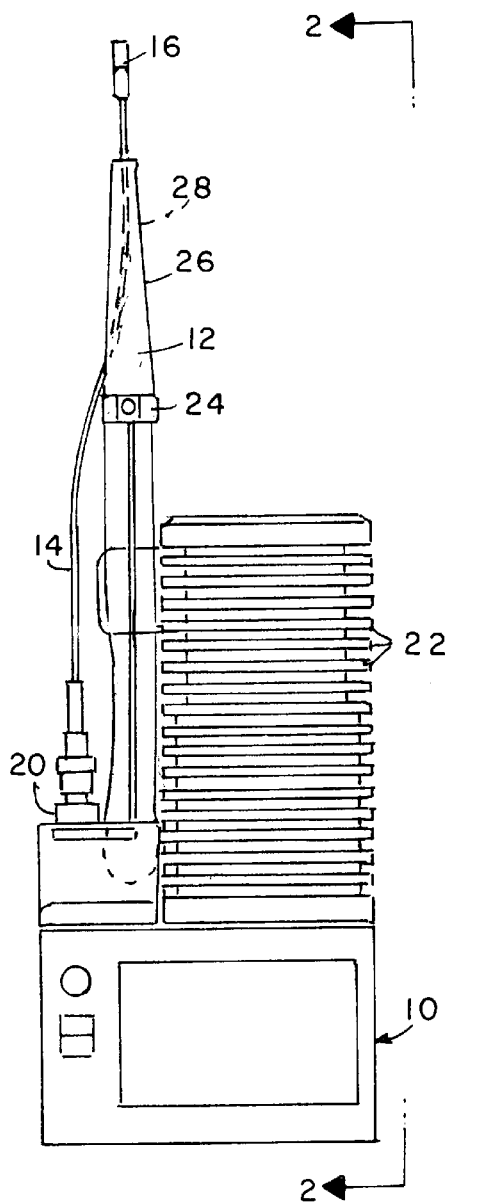
FIG. 1 is a side elevational view of a portable laser cautery system constructed according to the principles of the present invention.

Referring now to the drawings in detail, and particularly to FIG. 1, there is shown a housing 10 which contains efficient semiconductor laser generators for supplying laser energy to a medical instrument such as a forceps 12. The forceps 12 here are shown rigidly attached to the housing 10, coupled by an optical fiber conduit 14, to provide communication from the laser generating housing 10 to at least one tip 16 of the pair of tips 16 and 18 of the medical cautery forceps 12. The semiconductor lasers properly powered within the housing 10, may generate for example, between 0.5 W and 20 W of continuous wave (cw) laser power at a wavelength of for example, between 600 nm and 1500 nm. The lasers, not shown, within the housing, may consist of a single semiconductor laser element, an array of semiconductor lasers, several individual semiconductor lasers or a combination thereof. The laser energy generated by the semiconductor lasers is transmitted into the optical fiber conduit 14 through a connector 20 in the housing 10. The connector 20 may contain a single fiber or several optical fibers. In another preferred embodiment, the housing 10 may contain four fiber-coupled semiconductor lasers each delivering for example, 1.2 W cw of 810 nm laser energy out of a 150 $\mu$m diameter, 0.27 Numerical Aperture (NA) optical fiber. The optical fibers from such individual semiconductor lasers are then bundled together in a standard SMA connector 20. The housing 10 may also act as a heat-sink to dissipate any excess heat generated by the semiconductor lasers therewithin. Such excess heat may therefore be dissipated by natural air convection around an arrangement of fins 22 encircling the housing, as shown in FIGS. 1 and 2.

Figure 2:
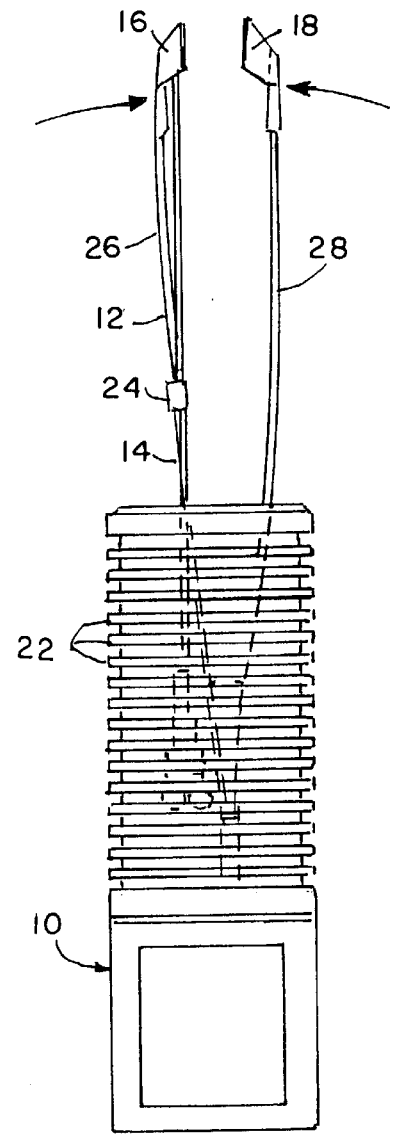
FIG. 2 is a view taken along the lines 2—2 of FIG. 1.

The semiconductor lasers disposed within the housing 10 in FIGS. 1 and 2, but not shown, may be powered by a battery through a current-control means. The battery may be rechargeable or disposable and may be a combination of several individual battery elements or a single battery element. The battery may be housed inside the protective housing 10, or be attached outside. In a preferred embodiment, five disposable Lithium batteries are used to provide a supply of 15 VDC with a capacity of 1 Ahr. The electric current supplied to the semiconductor lasers is regulated by a DC-DC converter-type electronic circuit, arranged within the housing 10. The circuit, not shown for clarity, is activated by a finger-switch 24 on one of the fingers 26 and 28 of forceps 12. Biasing of the fingers 26 and 28 together would provide the pressure against the finger switch 24.

Upon such switch 24 activation, the laser energy is then delivered through the optical fiber conduit 14 to at least one of the tip 16 and 18 of the medical forceps 12. The optical fiber conduit 14 may contain one or several optical fibers inside a protective sheath. In one preferred embodiment, the optical fiber conduit 14 is made of a single 600 $\mu$m diameter, 0.4 NA optical fiber comprising the conduit 14, disposed within a protective stainless-steel tubing 28, as shown in FIGS. 3, 4, 5 and 6. The tips 16 and 18 of the medical forceps 12 may be either permanently attached to or detachable from the heat sink fin arrangement of the housing 10. Such a detachable forceps 12 and conduit 14 arrangement is shown in FIG. 7.

Figure 3:
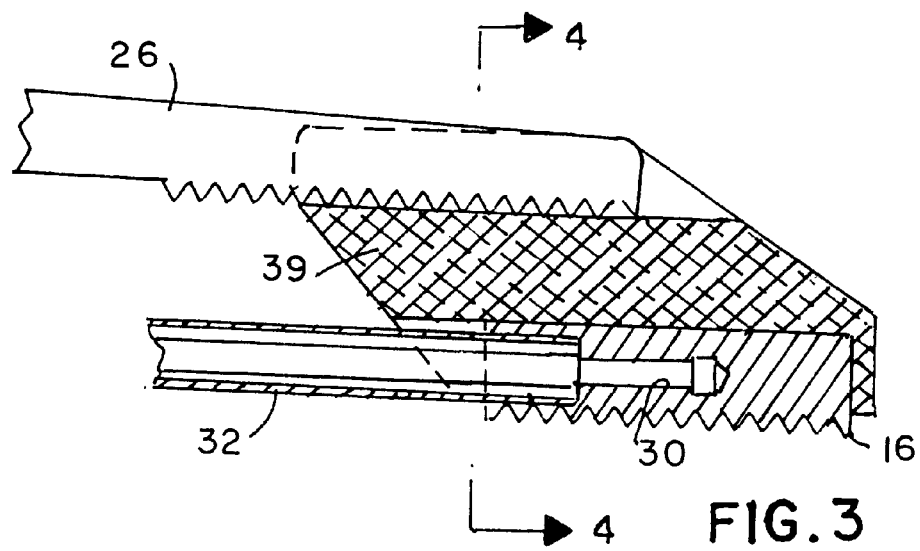
FIG. 3 is a side elevational view, in section, of a forceps tip of a laser cautery system constructed according to the principles of the present invention.
Figure 5:
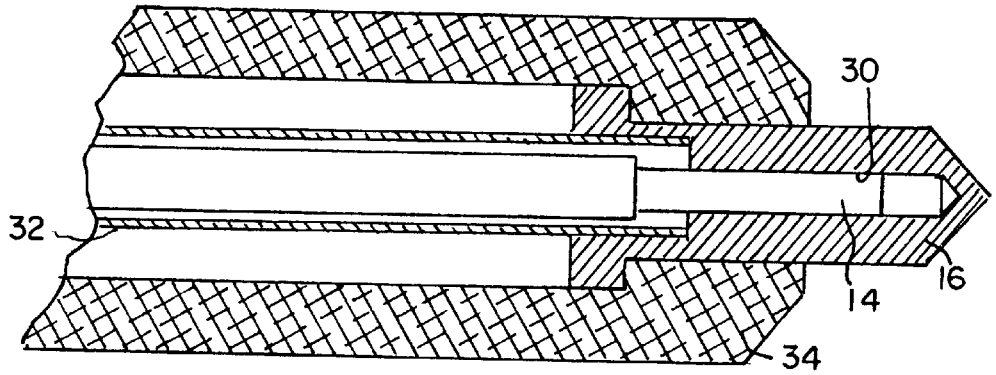
FIG. 5 is a side elevational view, in section, of a further embodiment of a tip of a cutting or dissecting instrument of the present invention.

In either the permanently attached, or the disattachable embodiment of the cautery forceps 12, at least the heated one of the tips 16 and 18 of the forceps 12 is designed to minimize its thermal mass. This "thermal" mass is defined by the product of mass of the tip 16 or 18 by its specific heat (or thermal capacity). In a preferred embodiment illustrated in FIG. 3, the tip 16 is made of a metal such as Titanium and for example, measures approximately 2 mm by 2 mm by 8 mm. The tip 16 has a small stepped bore 30, as shown in FIGS. 3 and 5, arranged so as to receive the optical fiber 14 through a protective stainless steel tube 32. This metal tip 16 may be coated with a hard PTFE or PFA Teflon coating to minimize the sticking of the cauterized tissue onto that tip 16. The tips 16 and 18 are mounted preferably using a high temperature epoxy such as TRA-BOND F202 or equivalent onto a thermal insulation block 34.

Figure 4:
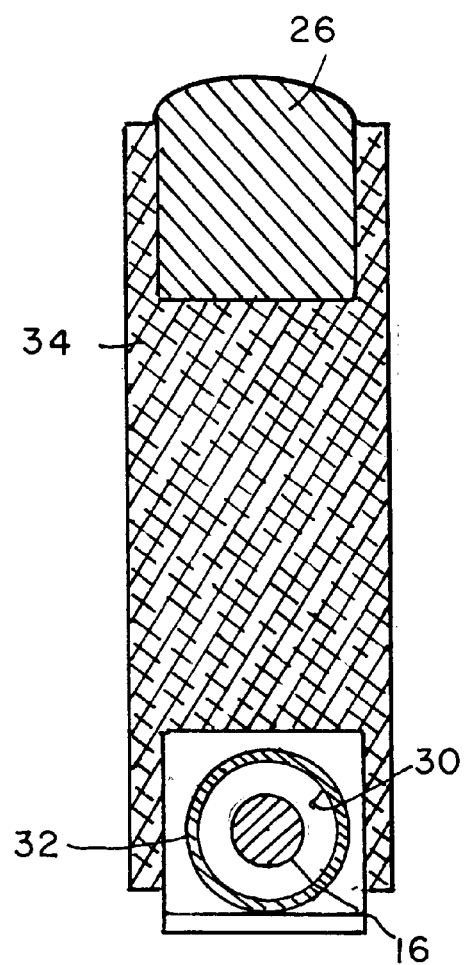
FIG. 4 is a view taken along the lines 4—4 of FIG. 2.

The insulating block 34 is made of a G10 material or other insulating material, providing a thermally insulated tip to the cautery device 12. The thermal insulation block 34 may also provide thermal insulation all around the tip 16, as shown in FIGS. 4 and 5, so as to prevent undesired thermal damage to surrounding tissues. This thermally insulated block 34, supporting the tip 16, is further mounted onto the finger(s) 26 and 28 of the medical forceps 12 using a similar epoxy bond or equivalent. The thermally insulated tips 16 and 18 may also be removable and disposable. The cautery forceps 12 may as aforesaid, have both tips 16 and 18 heated up simultaneously. In one preferred embodiment, as for example, as shown in FIG. 7, only one tip 16 in one finger 26 is attached to an optical fiber and therefore only this tip 16 is heated when the semiconductor lasers are activated. The second tip 18 and the second finger 28 is of the equivalent low thermal mass design to minimize heat losses through conduction when the fingers 26 and 28 of the forceps 12 are closed and both tips 16 and 18 are in contact with one another.

When the finger-switch 24 is depressed, the semiconductor lasers are activated and laser energy is delivered through the optical fiber conduit 14 to the energizable tip 16 of the medical forceps 12. Essentially all the laser energy is absorbed by the tip 16 and transformed into heat. Because of the inherent low thermal mass of the Titanium metal tip 16 and the heat losses by conduction being very small, the temperature of the tip 16 will increase very rapidly. The temperatures of the laser heated tip 16, when not in contact with anything, can reach of the order of about 200° C. within a few seconds. Such temperatures are sufficient to cauterize and weld together body tissue, including blood vessels, clamped between the fingers 26 and 28 of the medical forceps 12.

The device may be used to provide hemostasis in the human body during surgical procedures or in severe trauma situations. It is used by doctors, surgeons or other medical person in a manner similar to that of a bi-polar electrocautery device. After visual location of the bleeding site or blood vessel(s), the tissue surrounding the target site is grabbed and clamped between the tips 16 and 18 of the fingers 26 and 28 of the dedicated forceps 7. This provides temporary hemostasis at the targeted site. The forceps device 12 is then activated by depressing the finger switch 24 for a duration of typically 5 sec or until traditional visual clues such as local bubbling and popping around the tips 16 and 18 of the dedicated medical forceps 12 indicating that the targeted site is effectively cauterized. When the forceps device 12 is activated, the tip(s) 16 (and 18) of the dedicated medical forceps 12 is/are quickly heated up by laser energy heating the Titanium metal in which the distal end of such laser conduit 14 is embedded, as shown in FIGS. 3, 4 and 5. Subsequently the clamped tissue contained between the tips 16 and 18 of the dedicated medical forceps 12 is heated to such a temperature as to effectively cauterize and weld that tissue. This effectively closes all the vessels within the clamped area, and thus provides hemostasis at this site. The procedure can be repeated as many times as needed to stop all the bleeding sites. The procedure can also be repeated several times at the same site if necessary. The activation time can be increased or decreased to provide appropriate hemostasis at the targeted site. Larger vessels or more intense bleeding requires longer activation time.

Figure 6:
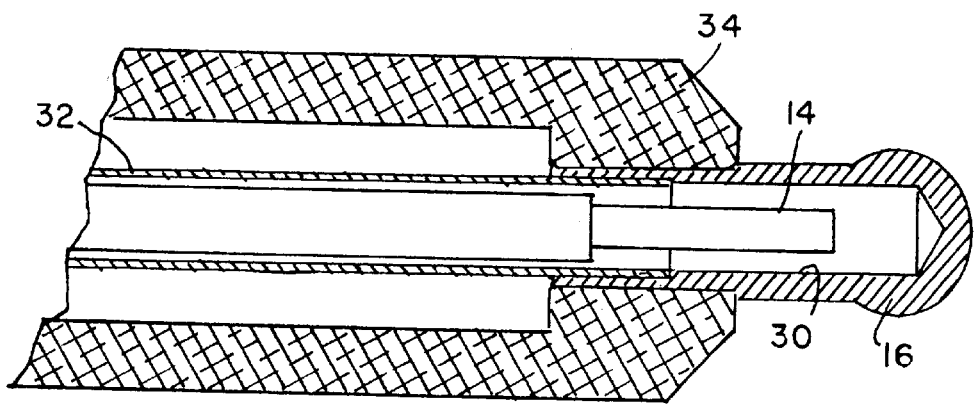
FIG. 6 is a side elevational view, in section, of a yet a still further embodiment of a tip of a coagulating instrument of the present invention.
Figure 7:
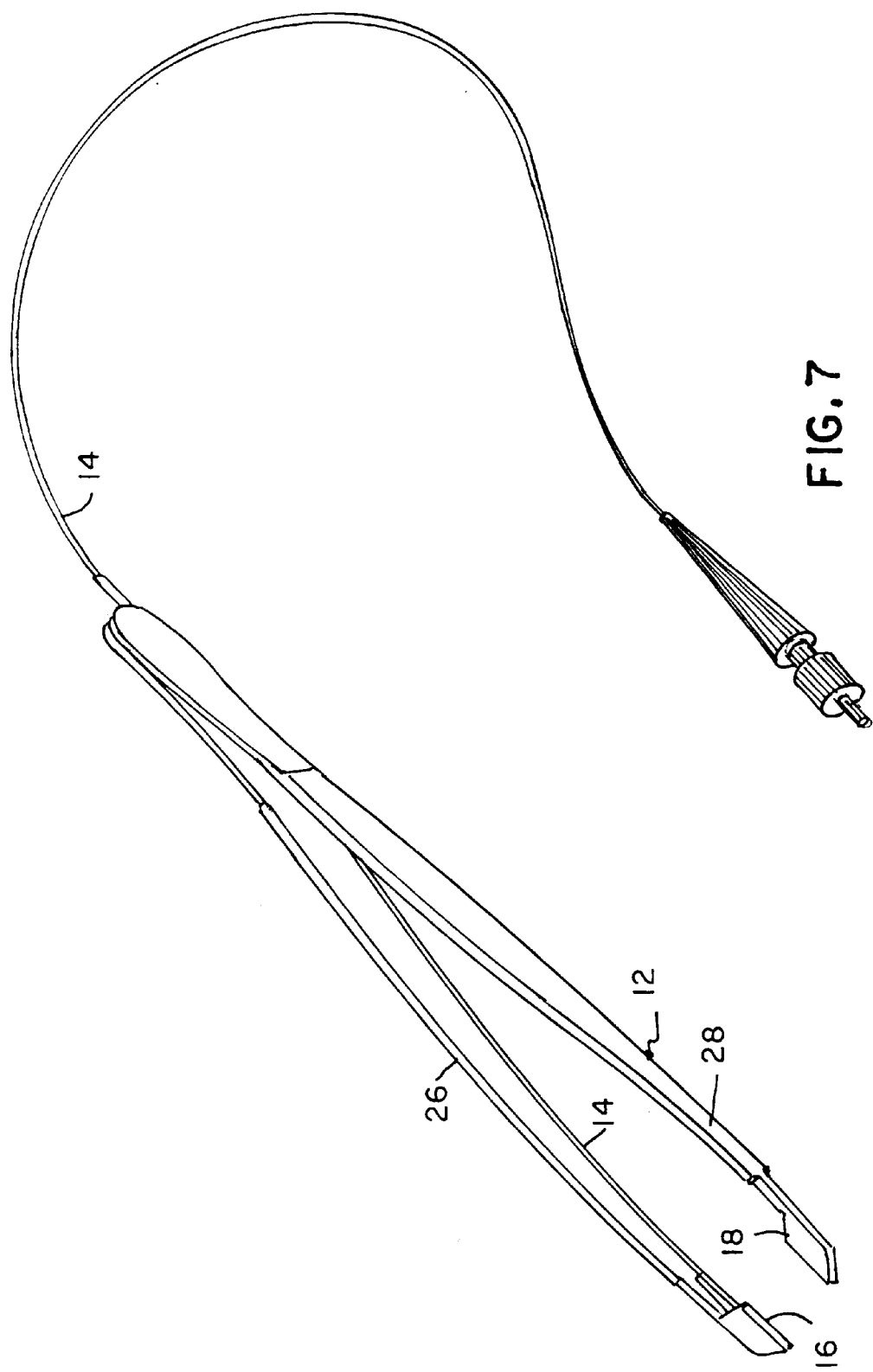
FIG. 7 is a schematic illustration of the invention showing a stand-alone fiber-coupled laser unit as a source of highly localized heat, the tip of the medical forceps being similar to the tip illustrated in FIG. 2.

Other embodiments are illustrated in FIGS. 5 and 6, which for clarity, shows only the tip of the inventive instruments. The body has been omitted, which body could have any shape or form. As described herinabove, such instrument may be connected to a housing 10 which contains efficient laser generators. In either a permanently connected or in a dis-connectable configuration, laser energy may be provided through the optical fiber conduit 14 to the energizable tip 16. The tip 16 is arranged to minimize thermal mass, and may be mountable on the insulating block 34. The tip 16 may also be coated with a hard PTFE or PFA Teflon® coating to minimize the sticking of heated tissue. When semiconductor lasers are activated, the temperature of the tip 16 increases very rapidly. In FIG. 5, the tip 16 preferably has a sharp edge or point. In this configuration, the tip temperature may be sufficient to vaporize the tissue in contact with the edge or point, thus providing the cutting action. Simultaneously, the tissue immediately adjacent to the edge or point of the tip 16 may be heated sufficiently to coagulate any potential bleeding. The tip 16 illustrated, may therefore be used to simultaneously cut and coagulate tissues. FIG. 6 shows a tip arranged with a broader and smoother surface. In this configuration, when the semiconductor lasers are activated, the surface of the tip 16 may reach a temperature sufficient to induce coagulation, of tissue touching the surface. The tip 16 shown in FIG. 6 may therefore be utilized to coagulate a superficially bleeding tissue or organ, i.e. a liver. The probe tips shown in FIGS. 3, 4, 5 and 6 each provide a closed housing for the distal tip of the laser conducting fiber optic strand or bundle 14. In FIG. 6, for example, the closed tip 16 has a central bore 30 into which the distal end of the optical conduit 14 is secured. The fiber or fiber bundle mat be secured within the tip with bushings or ferrules made of thermally insulating material, so that the fiber is held centrally disposed within the bore and aimed at the distal closed end of the bore. A protective metal tube 32 is securely attached to the probe tip 16 in a light proof manner to prevent leakage of laser light from the probe tip. A sufficient length along the coaxially common portions of the tip and the outer casing should be provided to minimize the chances of light leakage after repeated use or high mechanical stress during use.

We claim:

1. A thermo-coagulator system for the coagulation of body tissue to avoid direct delivery of optical energy to said body tissue, comprising:
   a medical instrument having a pair of biasable fingers, each of said fingers having a distal end with a metal tip secured thereon, at least one of said tips having a bore therein, said bore having an open end and an optical energy enclosing closed end;
   an optical conduit having a distal end arranged within said bore in said metal tip, said distal end of said optical conduit facing said closed end of said bore; and
   a source of optical energy coupled to said optical conduit to provide actuatable heat so as to raise the temperature of said metal tip on at least one of said fingers to permit said forceps to coagulate tissue.

2. The thermo-coagulator system for the coagulation of body tissue as recited in claim 1, wherein said source of optical energy comprises a laser generator.

3. The thermo-coagulator system as recited in claim 1, wherein said metal tip is disposed within an insulated jacket, said insulated jacket being attached to said distal end of said finger.

4. The thermo-coagulator system as recited in claim 1, wherein said fingers of said medical instrument each have a proximal end, each proximal end of said fingers being attached to a housing, said housing also enclosing said source of said optical energy.

5. The thermo-coagulator system as recited in claim 4, wherein said medical instrument are removable from said housing to permit said medical instrument free movement with respect to said housing.

6. The thermo-coagulator system as recited in claim 4, wherein said metal tips of said medical instrument are removable from said distal end of said fingers.

7. The thermo-coagulator system as recited in claim 1, wherein said tips of said medical instrument are made of Titanium metal.

8. The thermo-coagulator system as recited in claim 1, wherein said medical instrument is a forceps.

9. A method of providing hemostasis on body tissue using a thermo-coagulator device comprising the steps of:
   clamping the targeted blood vessels or body tissue between a pair of heatable metal tips of a forceps device; and
   heating only one of said metal tips of said forceps device by a supply of optical energy directed through a conduit from an energy generator into an optical energy enclosing bore in said only one metal tip, so as to avoid delivery of optical energy to sensitive body tissue during energization thereof.

10. The method of providing hemostasis on body tissue as recited in claim 9, including the step of:
    generating said heating of said metal tips in said forceps, by a laser pulse from a laser source, into said tips.

11. The method of providing hemostasis on body tissue as recited in claim 10, including the step of:
    directing said laser pulse through an optical fiber, which comprises said conduit.

12. The method of providing hemostasis as recited in claim 11, including the step of:
    absorbing the laser pulse in said metal tip; and
    converting said laser pulse into heat within said metal tip.

13. The method of providing hemostasis as recited in claim 12, including the steps of:
    attaching an insulative jacket to said metal tip, and attaching said insulative jacket to a distal end of a finger of said forceps device.

14. The method of providing hemostasis as recited in claim 13, including the steps of:
    energizing said forceps device by biasing said fingers of said device towards a tissue to be cauterized, so as to trigger a switch on said fingers during said biasing action.

* * * * *